(12) United States Patent
Chen

(10) Patent No.: US 9,102,962 B2
(45) Date of Patent: Aug. 11, 2015

(54) PRODUCTION METHOD FOR SOLID CULTURED ACTIVE MUSHROOM MYCELIUM AND FRUIT-BODY METABOLITES (AMFM) PRODUCTS THEREOF

(76) Inventor: Shiu Nan Chen, San Marino, CA (US)

( * ) Notice: Subject to any disclaimer, the term of this patent is extended or adjusted under 35 U.S.C. 154(b) by 1921 days.

(21) Appl. No.: 12/005,550

(22) Filed: Dec. 26, 2007

(65) Prior Publication Data
US 2009/0098620 A1   Apr. 16, 2009

Related U.S. Application Data

(60) Provisional application No. 60/999,298, filed on Oct. 16, 2007.

(51) Int. Cl.
*C12P 19/04* (2006.01)
*C12N 1/14* (2006.01)

(52) U.S. Cl.
CPC .. *C12P 19/04* (2013.01); *C12N 1/14* (2013.01)

(58) Field of Classification Search
CPC .................................. C12P 19/04; C12N 1/14
See application file for complete search history.

(56) References Cited

U.S. PATENT DOCUMENTS

| 6,041,544 A * | 3/2000 | Kananen et al. | |
| 2005/0097815 A1 * | 5/2005 | Wasser et al. | 47/1.1 |

FOREIGN PATENT DOCUMENTS

| JP | 51151319 A | * | 12/1976 |
| JP | 03098575 A | * | 4/1991 |
| JP | 2002218844 A | * | 8/2002 |
| JP | 2005065555 A | * | 3/2005 |
| JP | 2005102529 A | * | 4/2005 |
| JP | 2006111820 A | * | 4/2006 |
| KR | 2002001692 A | * | 1/2002 |

OTHER PUBLICATIONS

Stamets, P. International Journal of Medicinal Mushrooms (2003); 5:179-191. Potentiation of cell-mediatd host defenses using fruit bodies and mycelia of medicinal mushrooms.*
Ohno, N et al. Chemical and Pharmaceutical Bulletin (1985); 33(8): 3395-3401. Structural characterization and antitumor activity of the extracts from matted mycelium of culture *Grifola frondosa*.*

* cited by examiner

*Primary Examiner* — Michele Flood
(74) *Attorney, Agent, or Firm* — Raymond Y. Chan; David and Raymond Patent Firm

(57) ABSTRACT

A production method effectively increases the amount and yield of mushroom beta-glucan, and widely applied in the fields of food, biotechnology, cultivation and medical development. The cultivating medium contains the nutrition of three natural grains, including brown rice, adlay and oat, to provide a complete physiological environment for the mushrooms to grow well. Experimental results strongly suggest that AMFM treated cell activities are significantly enhanced in comparison with those without AMFM treated.

14 Claims, 2 Drawing Sheets

NK cell activity of AMFM-treated and control mice

Macrophage activity of AMFM treated and control mice

Glycosyl Linkage of AMFM Powder

| Results: | | |
|---|---|---|
| Glycosyl Linkage Analysis | | |
| | Glycosyl Residue | Percentage Present |
| PFO-021 | Terminally linked glucopyranosyl residue (t-Glc) | 23 |
| CY062206-1 | 3-linked glucopyranosyl residue (3-Glc) | 16.8 |
| | 2-linked glucopyranosyl residue (2-Glc) | 1.3 |
| | 3-linked galactopyranosyl residue (3-Gal) | 1.6 |
| | 6-linked glucopyranosyl residue (6-Glc) | 4.2 |
| | 4-linked glucopyranosyl residue (4-Glc) | 30.7 |
| | 3,4-linked galactopyranosyl residue (3,4-Gal) | trace |
| | 3,4-linked glucopyranosyl residue (3,4-Glc) | 14.7 |
| | 3,6-linked glucopyranosyl residue (3,6-Glc) | 3.6 |
| | 4,6-linked glucopyranosyl residue (4,6-Glc) | 2.5 |
| | 3,4,6-linked glucopyranosyl residue (3,4,6-Glc) | 1.6 |

PRODUCTION METHOD FOR SOLID CULTURED ACTIVE MUSHROOM MYCELIUM AND FRUIT-BODY METABOLITES (AMFM) PRODUCTS THEREOF

CROSS REFERENCE TO RELATED APPLICATION

This is a non-provisional application of a provisional application having an application No. 60/999,298 and a filing date of Oct. 16, 2007.

BACKGROUND OF THE PRESENT INVENTION

1. Field of Invention

The present invention relates to a production method for mushroom beta-glucan, and more particularly to the production method for mushroom mycelium and fruit-body metabolites products thereof, wherein the production method can effectively increase the amount and yield of mushroom beta-glucan, and widely applied in the fields of food, biotechnology, cultivation and medical development.

2. Description of Related Arts

Mushrooms are one of the most popular types of fungi, which are known to function without photosynthesis. Major nutrition types of fungi include saprophytic, adnascent and symbiotic. The mycelium bodies receive nutrients from soil or dead wood, and then congregate to form a fruit-body and generate spores for the purpose of reproduction.

Based on the features of mushroom growth, the cultivation methods can be roughly divided into four categories: (1) wood cultivation, products like tree mushrooms and mushrooms; (2) plastic-bag cultivation, products like lingzhi, tree mushrooms, mushrooms and Pleurotus eryngii; (3) auto-mechanical thermal control cultivation, products like *Flammulina velutipes, Agrocybe cylindracea* and *Hericium erinaceus*; (4) soil method, products like *Agaricus bisporus* and *Volvariella volvacea*.

There are various mushroom cultivation technologies for different kinds of mushrooms. Key factors such as temperature, humidity, light source and culture medium directly affect the growth of the mushrooms. During cultivation, mix fungus or insects may impede the growth of mushrooms. In addition, the stability of the mushroom strain is important because mushrooms are known to have mutations, so it is important to preserve the mushroom strains well and handle them with care.

In agriculture, mushroom fruit bodies are cultivated in plastic bags (plastic-bag cultivation). However, industrial pollution becomes more serious that causes too much heavy metal and chemicals left in the soil and water resources, such that the cultivating medium such as wood and soil is likely to be contaminated. Heavy metals are easy to be accumulated in mushrooms, so the source of cultivating medium has to be strictly screened.

SUMMARY OF THE PRESENT INVENTION

A primary object of the present invention is to provide a production method for solid cultured active mushroom mycelium and fruit-body metabolites (AMFM) products thereof, wherein grains and herbs are used as cultivating mediums and the cultivation environment is arranged to provide good air and light permeability by utilizing a specific-designed polycarbonate (PC) bottle.

Another object of the present invention is to provide a fungusless environment to isolated and prevent the pollution of mix fungus and harmful insects and to control the source and composition of the cultivating media so as to ensure the mushrooms having a good growing environment to retain a high quality for the mushroom products.

Another object of the present invention is to provide a cultivation environment with a specific-design cultivation bottle made of Polycarbonate (PC) material, wherein the PC bottle is light and impact-resistant, so as to allow people to easily carry and move, and save the labors. Furthermore, unlike glass materials, it is not easy to break due to slight collision. Also, the PC bottle is non-toxic and thermal resistant, such that the PC bottles can be placed under sterilization process without worrying about safety issues. The body of the PC bottle is transparent so as to allow the user to observe and allow extra illumination to stimulate mushroom's growth. The upper portion of the bottle has a shrink opening which can be covered with an air permeable silicon stop to keep the content in the PC bottle from any contamination, while the lower portion of the bottle has an enlarged base area to allow the mycelium to have enough surface area for air exchanging and enough space for fruit body's growth.

Another object of the present invention is to provide a production method for solid cultured active mushroom mycelium and fruit-body metabolites (AMFM) products thereof, wherein the nutrition of three natural grains helps mushrooms grow well. The natural grains are crumbled at the very beginning, then frozen and dried, and grinded into powders to preserve the beta-glucan and enzyme in mycelium, as well as triterpennoids and cellulose in fruit bodies, to compose a complete physiological environment.

Another object of the present invention is to provide a production method for solid cultured active mushroom mycelium and fruit-body metabolites (AMFM) products thereof, which nutritious mode can be applied to most mushrooms, wherein the adjustment of cultivating medium can induce mycelium to generate different kinds of metabolites. The present invention can be applied to microorganisms, such as yeast, fungus and natto, to manufacture metabolites through solid fermentation.

These and other objectives, features, and advantages of the present invention will become apparent from the following detailed description, the accompanying drawings, and the appended claims.

BRIEF DESCRIPTION OF THE DRAWINGS

FIG. 3 is a table illustrating the results of glycosyl linkage analysis for active mushroom mycelium and fruit-body (AMFM) extract powder.

DETAILED DESCRIPTION OF THE PREFERRED EMBODIMENT

Figure 1:
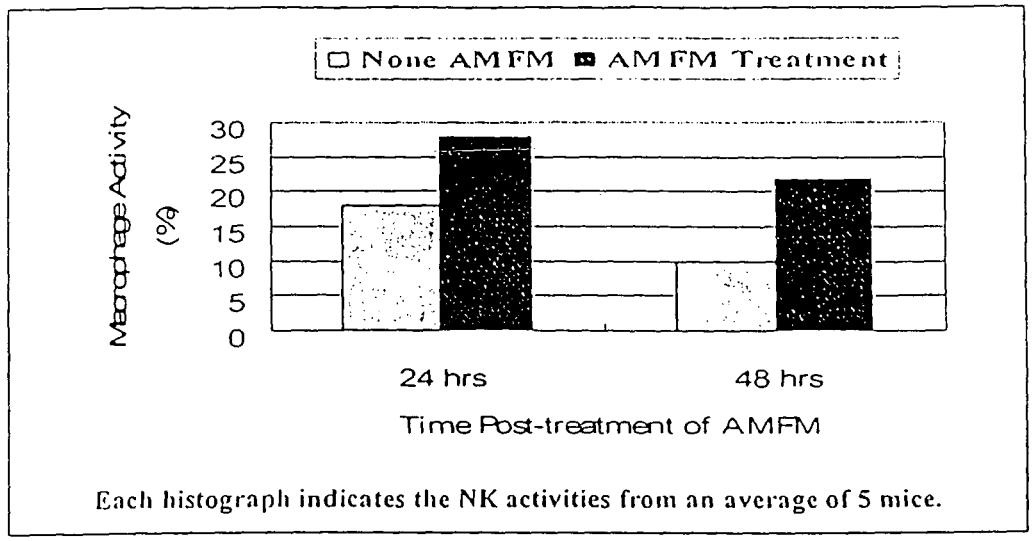
FIG. 1 is a diagram illustrating NK cell activity of AMFM treated and non AMFM-treated (controlled) mice.

According to a preferred embodiment of the present invention, which provides a method of producing mushroom beta-glucan, comprising the steps of:

(a) inoculating liquid cultivated mushroom with natural grains to grow mushroom mycelium as cultivating medium, wherein the natural grains selected from a group consisting of a mixture of brown rice, adlay and oat to provide a complete physiological environment for said mushroom mycelium to grow;

(b) dividing the mushroom mycelium into a first portion and a second portion;

(c) preserving the first portion of the mushroom mycelium;

(d) preserving the second portion of the mushroom mycelium with plant illumination to stimulate mycelium to generate first body; and (e) mixing the first and second portions of the mushroom mycelium to obtain mushroom beta-glucan.

According to a preferred embodiment of the present invention, in the step (a), brown rice (or hulled rice), adlay (or called Chinese pearl barley, Job's tears) and oat are mixed with equal weight respectively. 500 gram of the mixed grain mixture is transferred into a PC bottle which contains 500 gram reverse osmosis (RO) filtration water. Enclose the PC bottle with an air-permeable silica cover. Then the PC bottle is sterilized at 121° C. for 15 minutes. After cooling off from sterilization, 200-300 ml of liquid cultivated mushroom strains is inoculated into the PC bottle. Under room temperature, mushroom mycelium starts to grow in three to seven days and spreads to the entire cultivating medium after two weeks to one month. At this stage, in the step (b), the mycelium is divided into two portions. In the step (c), a first portion of the mushroom mycelium is removed from the PC bottle and frozenly preserved. In the step (d), a second portion of the mushroom mycelium remained in the PC bottle is preserved in a place having a temperature of about 15-20° C. or treated with plant illumination, in order to stimulate the mycelium to generate fruit body, wherein the second portion is further cultivated for two weeks to one month before removing from the PC bottle.

Afterwards, in the step (e), the second portion is removed from the PC bottle and mixed the first portion. Then, put the mixture under –40° C., 0.3 Mpa (Lyophilization) to condense to powder containing 5% water. The powders are further mixed and grinded into solid mushroom beta-glucan powders.

EXAMPLE 1

The results of glycosyl linkage analysis for active mushroom mycelium and fruit-body (AMFM) extract powders are described in the Table as shown in FIG. 3. The results indicate that the sample was mainly glucose polymer with 3;6;4-linked glycopyranosyl branches. The results obtained from analysis study may suggest that the AMFM product is an effective immkuo-modulator.

EXAMPLE 2

To evaluate the concentration of phagoeytosis of the AMFM product, synthetic microspheres based on 2-hydroxyethyl methacrylate copolymer are used. One experimental dose of the AMFM product (100 μg/mouse) is applied. A significant elevated level of phagocytosis of both neutrophilis and monocytes can be seen in three different time frames (the 24, 48 and 72 hour). The results show that the percentage of phagocytosing monocytes in peripheral blood increases from 30.6% to 40-45%, and the percentage of phagocytosing granulocytes increases from 27.1% to 38-42%. Based on the experimental data illustrated above, it is concluded that the test samples represent a highly active glucans.

EXAMPLE 3

In order to observe the activity of natural killer cells in vivo, the product, 100 μg of AMFM is orally inoculated into C57BL/$_6$ mice twice a day (at 9pm and 3am) for three consecutive days. After 24 to 48 hours post-treatment, the activity of natural killer cell from spleen of mice is then detected using Flowcytometry (PARTECGMBH, Germany). Totally, 20 mice are used for the experiment (10 mice for control; 10 for experiment) and the results are shown in FIG. 1. The results reveal that a significant NK activity was obtained in the experimental mice 24 to 48 hours post-treatment. It is suggested that oral AMFM product ingestion may effectively enhance cellular immunity of experimental mice.

EXAMPLE 4

Figure 2:
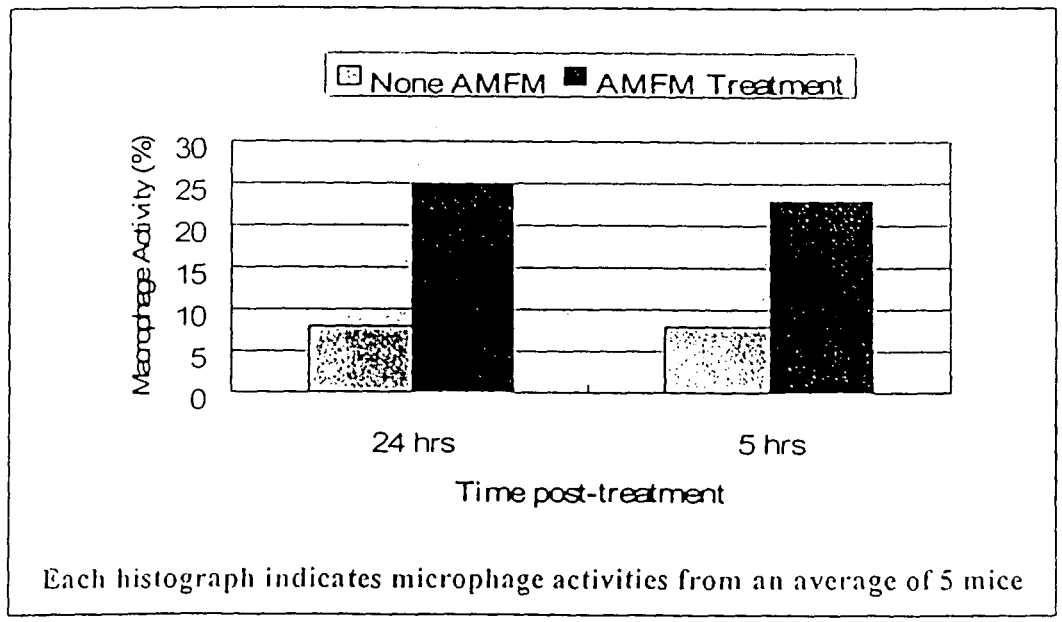
FIG. 2 is a diagram illustrating macrophage activity of AMFM treated and non-AMFM treated (controlled) mice.

To observe the effect of the AMFM product on the activities of macrophage, the experimental C57BL/$_6$ mice is orally inoculated with AMFM product at the dose of 100 μg/mouse twice a day (at 9pm and 3am) for three consecutive days. After 24 to 48 hours post-treatment, the mice are then sacrificed and the blood is collected for the analysis of macrophage activities using Flowcytometry (PARTECGMBH, Germany). The results presented in FIG. 2 show that macrophage activities derived from AMFM product treatment is significantly higher than those of non-AMFM or in control experiment. It is suggested that oral ingestion of AMFM product may significantly upgrade microphage of experimental mice.

It is worth to mention that, in conventional solid cultivation, the source of cultivating medium is not completely controllable, such that excessive amount of heavy metal is likely to accumulate in the fruit body of mushroom, and the adjustment of nutrition combination lacks flexibility because of the same reason. In the present invention, natural grains such as brown rice, adlay and oat are adapted to be the base of cultivating medium to provide nutrients to most mushrooms to generate metabolites, such as beta-glucan. Also, different types of mushroom may have different medium formulas, for example, adding animal protein as a nutrient can stimulate *Cordyceps militaris* to generate fruit body; adding wood flour or plant extraction liquid to increase the concentration of mycelium; adding legumes to facilitate isoflavones generation; or adding herbs to control the bio-activities of mushrooms.

The nutrition of three natural grains provided in the present invention helps mushrooms grow well. The natural grains are crumbled at the very beginning, then frozen and dried, and grinded into powders to preserve the beta-glucan and enzyme in mycelium, as well as triterpennoids and cellulose in fruit bodies, to compose a complete physiological environment.

The same nutritious mode can be applied to most mushrooms, wherein the adjustment of cultivating medium can induce mycelium to generate different kinds of metabolites. This invention can also be applied to microorganisms, such as yeast, fungus and natto, to manufacture metabolites through solid fermentation.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of producing mushroom beta-glucan, comprising the steps of:
   (a) growing mushroom mycelium as cultivating medium in a complete physiological environment by inoculating liquid cultivated mushroom with one or more natural grains, wherein said liquid cultivated mushroom is inoculated with said natural grains into a polycarbonate bottle which is enclosed with an air-permeable cover;
   (b) dividing said mushroom mycelium into a first portion and a second portion;
   (c) preserving said first portion of said mushroom mycelium;
   (d) preserving said second portion of said mushroom mycelium to generate first body; and
   (e) mixing said first portion and said first body of said mushroom mycelium to form a mixture and condensing said mixture to obtain mushroom beta-glucan, wherein said polycarbonate bottle has a shrunk opening covered with said air-permeable cover and an enlarged lower portion to provide enough surface area for air exchanging and for said mushroom mycelium to grow.

2. The method, as recited in claim 1, wherein in said step (e), said first body and said first portion of said mushroom mycelium are mixed and placed under −40° C., 0.3 Mpa through lyophilization to condense to powder containing 5% water.

3. The method, as recited in claim 1, wherein in said step (c), said first portion of said mushroom mycelium is frozenly preserved.

4. The method, as recited in claim 2, wherein in said step (c), said first portion of said mushroom mycelium is frozenly preserved.

5. The method, as recited in claim 1, wherein in said step (d), said second portion of said mushroom mycelium is preserved at about 15° C. to 20° C.

6. The method, as recited in claim 4, wherein in said step (d), said second portion of said mushroom mycelium is preserved at about 15° C. to 20° C.

7. The method, as recited in claim 1, wherein in said step (d), said second portion of said mushroom mycelium is preserved and treated with plant illumination.

8. The method, as recited in claim 4, wherein in said step (d), said second portion of said mushroom mycelium is preserved and treated with plant illumination.

9. The method, as recited in claim 4, after said step (e), further comprising a step of grinding said mushroom beta-glucan into a powder form.

10. The method, as recited in claim 6, after said step (e), further comprising a step of grinding said mushroom beta-glucan into a powder form.

11. The method, as recited in claim 8, after said step (e), further comprising a step of grinding said mushroom beta-glucan into a powder form.

12. The method, as recited in claim 2, before said step (a), further comprising the steps of:
    adding reverse osmosis filtration water into said polycarbonate bottle;
    sterilizing said polycarbonate bottle at 121° C. for approximately 15 minutes; and
    cooling down said polycarbonate bottle for said liquid cultivated mushroom with said natural grains being transferred to said polycarbonate bottle.

13. The method, as recited in claim 8, before said step (a), further comprising the steps of:
    adding reverse osmosis filtration water into said polycarbonate bottle;
    sterilizing said polycarbonate bottle at 121° C. for approximately 15 minutes; and
    cooling down said polycarbonate bottle for said liquid cultivated mushroom with said natural grains being transferred to said polycarbonate bottle.

14. The method, as recited in claim 11, before said step (a), further comprising the steps of:
    adding reverse osmosis filtration water into said polycarbonate bottle;
    sterilizing said polycarbonate bottle at 121° C. for approximately 15 minutes; and
    cooling down said polycarbonate bottle for said liquid cultivated mushroom with said natural grains being transferred to said polycarbonate bottle.

* * * * *